(12) United States Patent
Plos et al.

(10) Patent No.: US 7,192,455 B2
(45) Date of Patent: Mar. 20, 2007

(54) PROCESS FOR DYEING KERATIN FIBERS WITH AT LEAST ONE NINHYDRIN DERIVATIVE

(75) Inventors: Grégory Plos, Tokyo (JP); Luc Gourlaouen, Asnieres (FR)

(73) Assignee: L'Oreal S.A., Paris (FR)

( * ) Notice: Subject to any disclaimer, the term of this patent is extended or adjusted under 35 U.S.C. 154(b) by 386 days.

(21) Appl. No.: 10/898,369

(22) Filed: Jul. 26, 2004

(65) Prior Publication Data
US 2005/0050654 A1  Mar. 10, 2005
US 2006/0112499 A9  Jun. 1, 2006

Related U.S. Application Data

(60) Provisional application No. 60/499,454, filed on Sep. 3, 2003.

(30) Foreign Application Priority Data

Jul. 25, 2003 (FR) .................. 03 09174
Mar. 4, 2004 (FR) .................. 04 02241

(51) Int. Cl.
*A61K 7/13* (2006.01)
(52) U.S. Cl. ............... 8/405; 8/406; 8/407; 8/410; 8/411; 8/421; 8/607; 568/327
(58) Field of Classification Search ............ 8/405, 8/406, 407, 410, 411, 421, 607; 568/327
See application file for complete search history.

(56) References Cited

FOREIGN PATENT DOCUMENTS

| AU | 199911498 B2 | 5/1999 |
|---|---|---|
| DE | 43 17 855 | 12/1994 |
| DE | 4317855 A1 * | 12/1994 |
| DE | 197 17 222 A1 | 10/1998 |
| DE | 197 45 355 A1 | 4/1999 |
| DE | 198 45 481 A1 | 4/2000 |

OTHER PUBLICATIONS

English Abstract of the Patent No. DE 4317855 A1.*
STIC Search Report (Aug. 7, 2006).*
Cantu, A.A. et al., "Comparative Evaluation of Several Amino Acid Reagents for Visualizing Amino Acid (Glycine) on Paper", J. Forens. Ident. 1993, 43, 44-66.
Dallemagne P. et al., "Synthesis of Thianinhydrine, a Thiophenic Isoster of ninhydrin," Bull. Soc. Chim. Fr. 1991, 128, 260-266.
Khanh, L. et al., "First Synthesis of Isothianinhydrin, The Second Thiophene Isostere of Ninhydrin," Synlett, 1999, 9, 1450-1452.
Heffner R.J. et al., "A Synthesis of Two Novel Benzo[f]ninhydrin analogs: 6-methoxybenzol[f]ninhydrin and thieno[f]ninhydrin," Synth. Commun. 1991, 21 1055-1069.
Hauze D.B., Synthesis of Ninhydrin and Ninhydrin Analogs: Synthetic Efforts toward the Total Synthesis of a (3,4)-didehydroproline Analog of Astin G, Ph. D. dissertation Thesis, University of Pennsylvania, 1996.
Hauze D.b. et al., New Reagents For the Development of Fingerprints in Almog J. Springer E., ed. Proceedings of the International Symposium on Fingerprint Detection and Identificiation, Ne'urim, Israel: Hemed Press, 1995, 119-123.
English Language Derwent for DE 197 17 222 A1.
English Language Derwent for DE 198 45 481 A1.
Database WPI, Derwent Publications Ltd., London, GB; AN 1973-22659U '16! & JP 48 011956 B.
English language Derwent Abstract of DE 43 17 855, Dec. 1, 1994.

* cited by examiner

*Primary Examiner*—Eisa Elhilo
(74) *Attorney, Agent, or Firm*—Finnegan, Henderson, Farabow, Garrett, & Dunner, L.L.P.

(57) ABSTRACT

The present disclosure relates to a process for dyeing keratin materials with compositions comprising, in a medium that is suitable for dyeing, at least one ninhydrin derivative, which may optionally be combined with at least one compound comprising at least one labile hydrogen. Further disclosed herein are dying compositions, multi-component hair dye compositions, and a multi-compartment kits.

25 Claims, No Drawings

PROCESS FOR DYEING KERATIN FIBERS WITH AT LEAST ONE NINHYDRIN DERIVATIVE

This application claims benefit of U.S. Provisional Application No. 60/499,454, filed on Sep. 3, 2003.

The present disclosure relates to compositions for dyeing keratin materials, such as hair dye compositions comprising at least one ninhydrin derivative, which in some embodiments, may be combined with a compound comprising a primary or secondary amine functional group, or a compound comprising an activated methylene functional group. The present disclosure also relates to a dyeing process using such compositions and to a multi-component coloring agent for performing such a process.

Throughout the years, people have sought to modify the color of their skin, their eyelashes or their hair, for instance to mask their grey hair. Several techniques have been developed to do this.

It is known to dye human keratin fibers, such as the hair, with dye compositions comprising oxidation dye precursors, which are also known as oxidation bases. These oxidation bases are colorless or weakly colored compounds which, when combined with oxidizing products, give rise to colored compounds by a process of oxidative condensation. These dyes are insoluble and are trapped inside the hair fiber.

It is also known that it is possible to vary the shades obtained with these oxidation bases by combining them with couplers or coloration modifiers. The variety of molecules used as oxidation bases and couplers can allow a wide range of colors to be obtained.

The colorations obtained show good longevity (also referred to as color-fastness) with exposure to shampoo. However, the oxidation reaction takes place using oxidizing products such as aqueous hydrogen peroxide solution in a basic medium. These oxidizing agents attack the keratin of the hair, and can cause the cosmetic and mechanical properties of the keratin to become greatly degraded in the event of repeated colorations.

It is also known practice to dye human keratin fibers by direct dyeing, which comprises applying to the keratin fibers direct dyes, which are colored and dyeing molecules that have affinity for the fibers. Examples of direct dyes that are conventionally used include nitro dyes, benzene dyes, anthraquinone dyes, nitropyridine dyes, azo dyes, cationic azo dyes, xanthene dyes, acridine dyes, azine dyes, triarylmethane dyes or natural dyes.

The colorations thus obtained are quite chromatic and do not cause any chemical degradation of keratin. However, they can have the drawback of being only temporary or semi-permanent, i.e. the color may fade after only 4 to 5 shampoo washes.

A need therefore remains for dyeing systems and processes that can give color-fast results without involving the use of oxidizing agents that are liable to degrade the keratin materials.

Accordingly, one aspect of the present disclosure relates to the use of at least one ninhydrin derivative, as described in greater detail hereinbelow, to dye keratin fibers, such as the hair, with a color-fastness, and without the need for strong oxidizing agents, thus helping to keep the keratin materials intact.

The at least one ninhydrin derivative mentioned above may be used, for example, in combination with compounds comprising at least one labile hydrogen, such as primary or secondary amines or compounds comprising an activated methylene functional group.

The colors thus obtained can show good chromaticities and can also, for instance, exhibit excellent color-fastness, for example, lasting through several tens of shampoo washes.

One aspect of the present disclosure is thus a process for dyeing keratin materials comprising applying to the keratin materials a composition comprising, in a medium that is suitable for dyeing, at least one ninhydrin compound of formula (I) or the tautomer thereof:

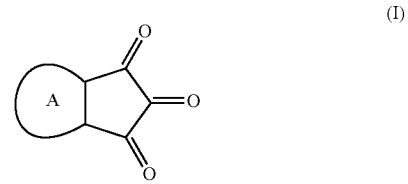

wherein

A is chosen from fused and non-fused, aromatic mono- and polyheterocyclic groups comprising at least 5-members, and comprising at least one hetero atom chosen from nitrogen, oxygen, sulfur and phosphorus.

This aromatic heterocyclic group A can optionally be substituted with at least one entity chosen from halogens, such as chloro, iodo, bromo and/or fluoro, $C_1$–$C_6$ alkyl radicals, hydroxyl radicals, $C_1$–$C_6$ alkoxy radicals, amino radicals, imidazolyl radicals, pyridyl radicals, mono- and di($C_1$–$C_6$ alkyl)amino radicals, mono- and dihydroxy($C_1$–$C_6$ alkyl)amino radicals, tri($C_1$–$C_6$ alkyl)ammonio radicals, thio radicals, ($C_1$–$C_6$ alkyl)thio radicals, thio($C_1$–$C_6$ alkyl) radicals, ($C_1$–$C_6$ alkyl)carbonyl radicals, hydrogenocarbonyl radicals, hydroxycarbonyl radicals, ($C_1$–$C_6$ alkoxy)carbonyl radicals, nitro radicals, sulphonato radicals and the corresponding protonated groups such as ammonio, imidazolio and/or pyridinio.

Such compositions are useful, for instance, for dyeing keratin fibers, such as the hair.

In one embodiment of the present disclosure, A is chosen so as to form with the indanetrione nucleus a system comprising delocalized π electrons.

As used in the present disclosure, any reference to the compounds of formula (I) also includes, of course, the corresponding acid addition salts and addition salts with bases.

The ninhydrin derivatives of formula (I) above are used according to the present disclosure, for example, in a cosmetically acceptable medium, which can comprise a large fraction of water. When they are dissolved in such an aqueous medium, the ninhydrin derivatives of formula (I) are in hydration equilibrium with the gem-diol (or carbonyl hydrate) form of formula (Ia) below:

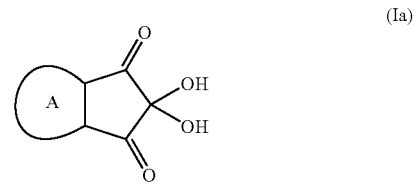

Thus, as disclosed herein, when ninhydrin derivatives of formula (I) are referenced, such references always include not only the compounds of formula (I) but also the corresponding hydrated forms of formula (Ia).

Non-limiting examples of ninhydrin derivatives that may be used according to the present disclosure for dyeing keratin fibers, for instance, include:

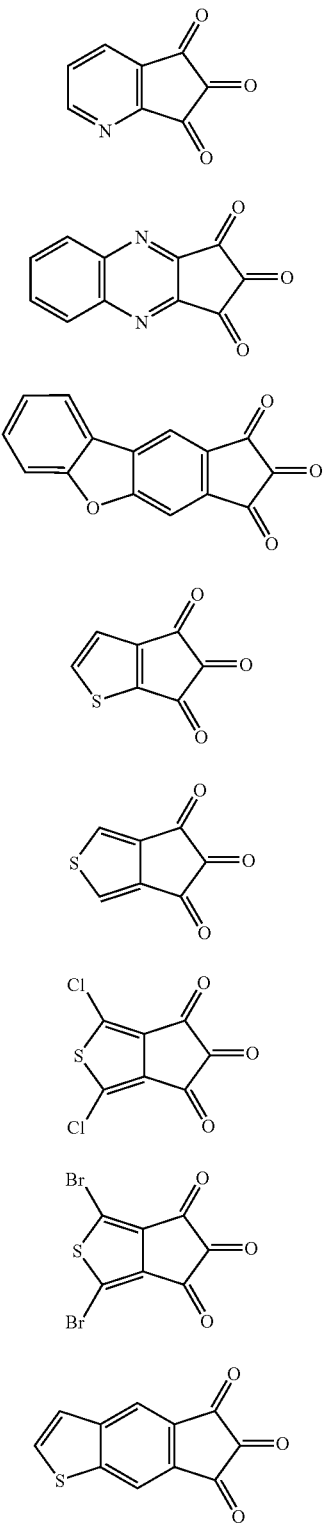

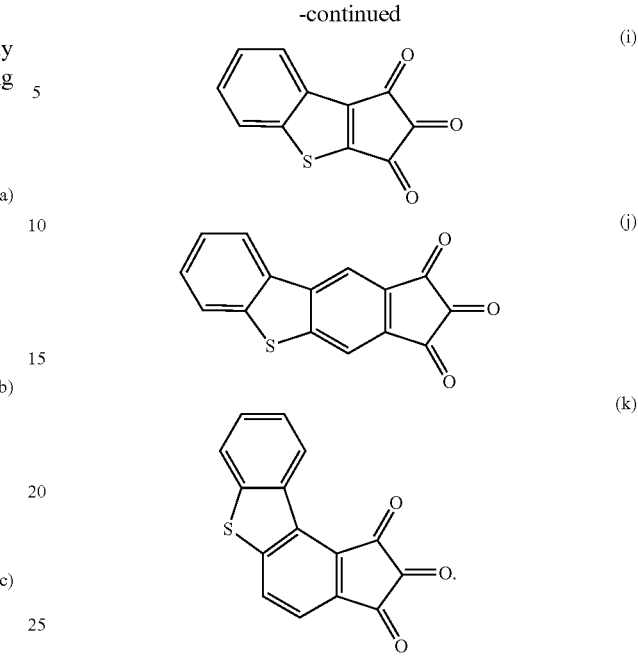

In one embodiment, the ninhydrin derivatives used as disclosed herein are known. The synthesis of the above ninhydrin derivatives (a) to (k) is described in the following publications:

(a) Cantu A. A., Leben D. A., Joullie M. M., Heffner R. J., Hark R. R., *A comparative evaluation of several amino acid reagents for visualizing amino acid (glycine) on paper*, J. Forens. Ident. 1993, 43, 44–66

(d) Dallemagne P., Rault S., Robba M., *Synthesis of thianinhydrine, a thiophenic isostere of ninhydrin*, Bull. Soc. Chim. Fr. 1991, 128, 260–266

(e) Khanh L., Dallemagne P., Rault S., *First synthesis of isothianinhydrin, the second thiophene isostere of ninhydrin*, Synlett, 9, 145–1452 ( )

(f) Hauze D. B., *Synthesis of ninhydrin and ninhydrin analogs: synthetic efforts toward the total synthesis of a (3,4)-didehydroproline analog of astin G*, Ph. D. dissertation Thesis, University of Pennsylvania, 1996

(g) Khanh L., Dallemagne P., Rault S., *First synthesis of isothianinhydrin, the second thiophene isostere of ninhydrin*, Synlett, 9, 145–1452 ( )

(h) Heffner R. J., Joullié M. M., *A synthesis of two novel benzo[f]ninhydrin analogs: 6-methoxybenzo[f]ninhydrin and thieno[f]ninhydrin*, Synth. Commun. 1991, 21, 1055–1069

(i) Hauze D. B., *Synthesis of ninhydrin and ninhydrin analogs: synthetic efforts toward the total synthesis of a (3,4)-didehydroproline analog of astin G*, Ph. D. dissertation Thesis, University of Pennsylvania, 1996

(j) Hauze D. B., Petrovskaia O., Joulliée M. M., Hark R. R., *New reagents for the development of fingerprints in Almog J.*, Springer E., ed. Proceedings of the International Symposium on Fingerprint Detection and Identification, Ne'urim, Israel: Hemed Press, 1995, 119–123

(k) Hauze D. B., Petrovskaia O., Joulliee M. M., Hark R. R., *New reagents for the development of fingerprints in Almog J.*, Springer E., ed. Proceedings of the International Symposium on Fingerprint Detection and Identification, Ne'urim, Israel: Hemed Press, 1995, 119–123

In accordance with the present disclosure, the ninhydrin derivatives of formula (I) described above may be used alone for dyeing keratin materials. The reason for this, without being bound by theory, is that these compounds are capable of generating colored molecules with the amine functional groups of keratin, i.e., colored reaction with the keratin.

Compounds of formula (I) may also be used in combination with at least one activator, which makes it possible to modify the reaction kinetics of the ninhydrin compound with the keratin material. Such an activator may be, for example, chosen from oxidizing agents, reducing agents, Brönstedt acids, metal catalysts such as catalysts based on a transition metal such as iron, platinum or palladium, proteins, for instance enzymes, compounds that modify the ionic strength of the medium, such as NaCl salts, compounds comprising at least one labile hydrogen chosen from those comprising a primary or secondary amine functional group and those comprising an activated methylene functional group. Needless to say, a mixture of such compounds may also be used.

In another embodiment of the present disclosure, the compounds comprising a primary amine or secondary amine functional groups are, for example, chosen from aromatic amines.

Among the examples of aromatic amines that may be used according to the present disclosure, non-limiting mention may be made of N,N-dimethyl-p-phenylenediamine, N,N-diethyl-p-phenylenediamine, N-(2-hydroxyethyl)-N-ethyl-p-phenylenediamine, N,N,-bis(2-hydroxyethyl)-p-phenylenediamine, N-(2-methoxyethyl)-p-phenylenediamine, 2,3-, 2,4- or 2,5-dichloro-p-phenylenediamine, 2-chloro-p-phenylenediamine, 2,5-dihydroxy-4-morpholinoaniline dihydrobromide, 2-, 3- or 4-aminophenol, 2-aminomethyl-4-aminophenol, 2-hydroxymethyl-4-aminophenol, ortho-phenylenediamine, p-phenylenediamine, ortho-toluenediamine, 2,5-diaminotoluene, 2,5-diaminophenol, 2,5-diaminophenethol, 4-amino-3-methylphenol, 2-(2,5-diaminophenyl)ethanol, 2,4-diaminophenoxyethanol, 2-(2,5-diaminophenoxy)ethanol, 4-methylaminoaniline, 3-amino-4-(2'-hydroxyethyloxy)aniline, 3,4-methylenediaminoaniline, 3,4-methylenedioxyaniline, 3-amino-2,4-dichlorophenol, 4-methylaminophenol, 2-methyl-5-aminophenol, 3-methyl-4-aminophenol, 2-methyl-5-(2-hydroxyethylamino)phenol, 6-methyl-3-amino-2-chlorophenol, 2-methyl-5-amino-4-chlorophenol, 3,4-methylenedioxyphenol, 5-(2-hydroxyethylamino)4-methoxy-2-methylphenol, 4-amino-2-hydroxymethylphenol, 1,3-diamino-2,4-dimethoxybenzene, 2-, 3- or 4-aminobenzoic acid, 2-amino-, 3-amino- or 4-aminophenylacetic acid, 2,3-, 2,4-, 2,5-, 3,4- or 3,5-diaminobenzoic acid, 4-amino- or 5-aminosalicylic acid, 3-amino-4-hydroxybenzoic acid, 4-amino-3-hydroxybenzoic acid, 2-amino, 3-amino- or 4-aminobenzenesulphonic acid, 3-amino-4-hydroxybenzenesulphonic acid, 4-amino-3-hydroxynaphthalene-1-sulphonic acid, 6-amino-7-hydroxynaphthalene-2-sulphonic acid, 7-amino-4-hydroxynaphthalene-2-sulphonic acid, 4-amino-5-hydroxynaphthalene-2,7-disulphonic acid, 3-amino-2-naphthoic acid, 3-aminophthalic acid, 5-aminoisophthalic acid, 1,3,5-triaminobenzene, 1,2,4-triaminobenzene, 1,2,4,5-tetraminobenzene, 2,4,5-triaminophenol, pentaminobenzene, hexaminobenzene, 2,4,6-triaminoresorcinol, 4,5-diaminopyrocatechol, 4,6-diaminopyrogallol, 3,5-diamino-4-hydroxypyrocatechol, and aromatic anilines and aromatic phenols comprising another aromatic residue, of formula (II)

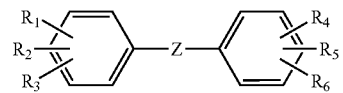

wherein:

$R_1$ is chosen from hydroxyl and amino radicals optionally substituted with a radical chosen from $C_{1-4}$ alkyl radicals, $C_{1-4}$ hydroxyalkyl radicals and ($C_{1-4}$ alkoxy)($C_{1-4}$ alkyl) radicals, $R_2$, $R_3$, $R_4$, $R_5$ and $R_6$, which may be identical or different, are chosen from hydrogen atoms, hydroxyl radicals and aminoradicals, optionally substituted with a radical chosen from $C_{1-4}$ alkyl, $C_{1-4}$ hydroxyalkyl, ($C_{1-4}$ alkoxy)($C_{1-4}$ alkyl), carboxylic acid, and sulphonic acid radicals, Z is chosen from a direct bond, saturated and unsaturated $C_{1-4}$ hydrocarbon radicals that may be optionally hydroxylated, carbonyl, sulphonyl and imino radicals, oxygen and sulfur atoms, radicals of formula Q-(CH$_2$—P—CH$_2$-Q')$_o$, wherein "$o$" is a number ranging from 1 to 4, P is chosen from a direct bond and —CH$_2$— and —CHOH— radicals, Q and Q', which may be identical or different, are chosen from oxygen atoms, NR$^7$ radicals wherein R$^7$ is chosen from a hydrogen atom, $C_{1-4}$ alkyl and $C_{1-4}$ hydroxyalkyl radicals; and O—(CH$_2$)$_p$NH and NH—(CH$_2$)p'—O radicals, wherein p and p' are equal to 2 or 3.

The non-aromatic primary or secondary amines may be chosen from, for example, 2-aminoethanol, 2-methoxyethylamine, 2-ethoxyethylamine, 2-(2-aminoethoxy)ethanol, 2- or 3-aminopropanol, 2,3-dihydroxypropylamine, 4-hydroxypropylamine, 2-aminopropane-1,3-diol, 2-amino-2-methylpropanol, 2-amino-2-methyl propane-1,3-diol, 2-amino-2-hydroxymethylpropane-1,3-diol, tetrahydropentylamine, pentahydroxyhexylamines such as glucamine, D-glucosamine, D-galactosamine, 1,2-diaminoethane, 1,2- or 1,3-diaminopropane, 1,3-diamino-2-propanol, 2-(2-aminoethylamino)ethylamine, 2-(2-aminoethylamino)ethanol, 3-(2-aminoethylamino)propylamine, and 3-(2-aminoethylamino)propanol.

The compounds comprising an activated methylene functional group may be chosen, for example, from 1,2,3,3-tetramethyl-3H-indolium iodide, 1,2,3,3-tetramethyl-3H-indolium p-toluenesulphonate, 1,2,3,3-tetramethyl-3H-indolium methanesulphonate, 1,3,3-trimethyl-2-methyleneindoline, 2,3-dimethylbenzothiazolium iodide, 2,3-dimethylbenzothiazolium p-toluenesulphonate, rhodanine, rhodanine-3-acetic acid, 1-ethyl-2-quinaldinium iodide, 1-methyl-2-quinaldinium iodide, barbituric acid, thiobarbituric acid, 1,3-dimethylthiobarbituric acid, diethylthiobarbituric acid, oxindole, 3-indoxyl acetate, coumarone and 1-methyl-3-phenyl-2-pyrazolinone.

Some primary and secondary amines and some compounds comprisiing activated methylene functional groups, as well as other compounds comprising at least one labile hydrogen, are described also in the German Patent Application Nos. DE 43 17 855, DE 197 17 222, DE 198 45 481 and DE 197 45 355, in which they are used for dyeing keratin fibers in combination with compounds other than the ninhydrin derivatives of formula (I).

In one embodiment, when the ninhydrin derivatives of formula (I) are used in combination with a composition comprising primary or secondary amine functional groups, or with a compound comprising an activated methylene functional group, it is necessary for these various reagents to be stored separately in order to avoid a premature color reaction. The reagents are in such an embodiment placed in contact only immediately before application to the hair, by extemporaneous mixing of two compositions comprising, respectively, at least one ninhydrin derivative and the compounds containing labile hydrogen. The reagents may also be combined directly on the hair by successive application of the various reagents.

Another aspect of the present disclosure is a multi-component hair coloring agent comprising at least one first component comprising a composition comprising at least one ninhydrin derivative of formula (I), and at least one second component comprising a composition comprising at least one entity chosen from compounds comprising a primary or secondary amine functional group and compounds comprising an activated methylene functional group, as described above.

This multi-component hair coloring agent may be provided, for example, as a multi-compartment kit, with at least one first compartment comprising at least one component and at least one second compartment comprising at least one second component.

Yet another aspect of the present disclosure is a cosmetic composition comprising at least one ninhydrin derivative of formula (I) and at least one compound chosen from surfactants and/or polymers, wherein the surfactants and/or polymers may be of nonionic, cationic, anionic and amphoteric nature.

Still another aspect of the present disclosure is a cosmetic dye composition comprising at least one ninhydrin derivative of formula (I) and at least one cosmetic active ingredient.

The cosmetic active ingredients that may be present in the cosmetic compositions as disclosed herein may be chosen, for example, from vitamins; saccharides; oligosaccharides; hydrolyzed and non-hydrolyzed, modified and unmodified polysaccharides; amino acids; oligopeptides; peptides; hydrolyzed and non-hydrolyzed, modified and unmodified proteins; polyamino acids; enzymes; branched and unbranched fatty acids and fatty alcohols; animal, plant and mineral waxes; ceramides and pseudoceramides; hydroxylated organic acids; UV-screening agents; antioxidants; free-radical scavengers; chelating agents; antidandruff agents; seborrhoea regulators; calmatives; cationic, anionic, nonionic and amphoteric surfactants; cationic, anionic, neutral and amphoteric polymers; organomodified and non-organomodified silicones; mineral, plant and animal oils; polyisobutenes, and poly($\alpha$-olefins); fatty esters, anionic polymers in dissolved and dispersed form; nonionic polymers in dissolved and dispersed form; reducing agents; solvents; hair dyes such as direct dyes and oxidation dye precursors (bases and/or couplers) other than the claimed compounds comprising a primary or secondary amine functional group; oxidizing agents such as hydrogen peroxide optionally combined with persalts; pigments; and mixtures thereof.

The at least one cosmetic active ingredient, when it is present, may be present in an amount ranging from 0.001% to 50% by weight, for instance, from 0.01% to 20% by weight, such as from 0.1% to 10% by weight, relative to the total weight of the cosmetic composition.

In one embodiment of the cosmetic dye composition according to the present disclosure, for example, the cosmetic active ingredient is chosen from surfactants and polymers, which may be of nonionic, cationic, anionic or amphoteric nature.

In a further embodiment, the hair dye compositions according to the present disclosure are stable during storage when they comprise, as sole reagents, at least one ninhydrin derivative of formula (I). However, when the compositions comprise both at least one ninhydrin derivative of formula (I) and at least one compound comprising labile hydrogen such as primary or secondary amines or compounds comprising an activated methylene functional groups, these compositions are generally used immediately after mixing the composition comprising the at least one ninhydrin derivative of formula (I) with those comprising at least one compound comprising labile hydrogen.

The ready-to-use dye compositions, whether they are being stored or prepared immediately before use, can have a pH ranging from 2 to 12, such as ranging from 3 to 11.

The at least one ninhydrin derivative of formula (I) can be present in an amount ranging from 0.0001% to 30% by weight, relative to the total weight of the composition.

The compounds comprising labile hydrogen used in combination with the at least one ninhydrin derivative of formula (I) can be present, for example, in an amount ranging from 0.0001% to 30% by weight, relative to the total weight of the composition.

Another aspect of the present disclosure is a ready-to-use cosmetic composition comprising at least one ninhydrin derivative of formula (I) and at least one compound comprising a primary or secondary amine functional group or at least one compound comprising an activated methylene functional group, or mixtures thereof.

Still another aspect of the present disclosure is a hair dyeing process comprising the application to the hair of a ready-to-use hair dye composition as described above. This composition is left in contact with the hair fibers for a period of time that is sufficient to obtain the desired coloration. This leave-in time ranges from 5 minutes to 1 hour, for instance, from 15 to 30 minutes. The color reaction between the at least one ninhydrin derivative and the amine functional groups of the keratin or of the compounds containing labile hydrogen that may optionally be present, may be accelerated by heating the hair impregnated with the dye composition. The heating temperature can be less than or equal to 80° C., such as less than or equal to 60° C.

After obtaining the desired coloration, the hair is rinsed and washed.

When compounds comprising labile hydrogen such as primary or secondary amines or compounds comprising an activated methylene functional group are used, the application of the reagents participating in the color reaction may also take place in two stages, in other words, two different compositions comprising, respectively, at least one ninhydrin derivative of formula (I) and at least one compound comprising a primary or secondary amine functional group or an activated methylene functional group may be applied successively.

Yet another aspect of the present disclosure is a two-stage dyeing process comprising the application to the hair one after the other, in any order, of a composition comprising at least one ninhydrin derivative of formula (I) and a composition comprising at least one entity chosen from compounds comprising a primary or secondary amine functional group or compounds comprising an activated methylene functional group. This separate application of two reactive compositions has the advantage of avoiding the handling of colored compositions and thus reduces the risks of soiling materials such as clothing.

Satisfactory hair colorations are also obtained when an intermediate rinsing step is inserted between the application of the first composition and the application of the second composition.

In a similar manner at that described above, the hair impregnated with either one of the at least two compositions of the multicomponent dyeing process may be heated, for example, at a temperature less than or equal to 80° C., such as a temperature less than or equal to 60° C., such heating making it possible to accelerate the color reaction and to shorten the leave-in time.

Other than where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches. Any numerical value, however, inherently contain certain errors necessarily resulting from the standard deviation found in their respective testing measurements.

What is claimed is:

1. A process for dyeing keratin materials comprising, applying to the keratin materials a composition comprising, in a medium that is suitable for dyeing, at least one ninhydrin compound of formula (I) or the tautomer thereof:

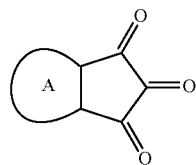

(I)

wherein:
A is chosen from fused and non-fused, aromatic mono- and polyheterocyclic groups comprising at least 5-members, and at least one hetero atom chosen from nitrogen, oxygen, sulfur and/or phosphorus.

2. The process according to claim 1, wherein the at least one ninhydrin compound of formula (I) is chosen from:

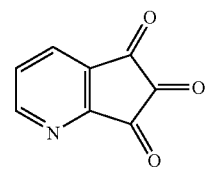

(a)

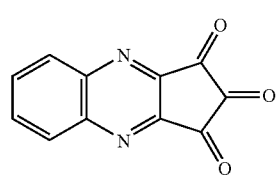

(b)

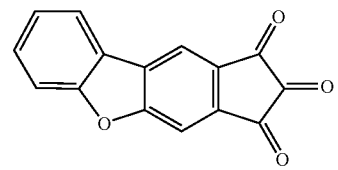

(c)

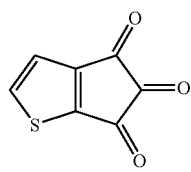

(d)

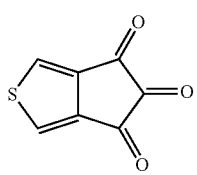

(e)

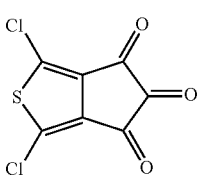

(f)

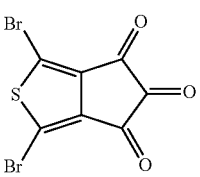

(g)

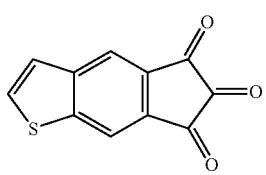

(h)

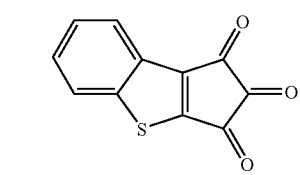

(i)

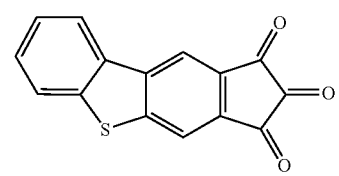

(j)

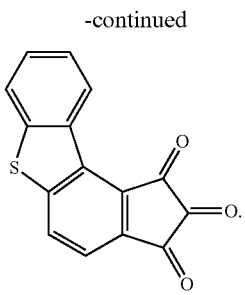

(k)

3. The process according to claim 2, wherein A is substituted with at least one entity chosen from halogens, $C_1$–$C_6$ alkyl radicals, hydroxyl radicals, $C_1$–$C_6$ alkoxy radicals, amino radicals, imidazolyl radicals, pyridyl radicals, mono- and di($C_1$–$C_6$ alkyl)amino radicals, mono- and dihydroxy ($C_1$–$C_6$ alkyl)amino radicals, tri($C_1$–$C_6$ alkyl)ammonio radicals, thio radicals, ($C_1$–$C_6$ alkyl)thio radicals, thio($C_1$–$C_6$ alkyl) radicals, ($C_1$–$C_6$ alkyl)carbonyl radicals, hydrogenocarbonyl radicals, hydroxycarbonyl radicals, ($C_1$–$C_6$ alkoxy) carbonyl radicals, nitro radicals, sulphonato radicals, and the corresponding protonated radicals.

4. The process according to claim 3, wherein the protonated radicals are chosen from ammonio, imidazolio and/or pyridinio radicals.

5. The process according to claim 1 wherein the composition applied to the hair further comprises at least one activator that makes it possible to modify the reaction kinetics of the at least one compound of formula (I) with the keratin material.

6. The process according to claim 5, wherein the at least one activator is chosen from oxidizing agents, reducing agents, Broñsted acids, metal catalysts, proteins, compounds that modify the ionic strength of the medium, and compounds comprising at least one labile hydrogen chosen from those comprising a primary or secondary amine functional group and those comprising an activated methylene functional group.

7. The process according to claim 6, wherein the at least one compound comprising a primary or secondary amine functional group is an aromatic amine chosen from N,N-dimethyl-p-phenylenediamine, N,N-diethyl-p-phenylenediamine, N-(2-hydroxyethyl)-N-ethyl-p-phenylenediamine, N,N,-bis(2-hydroxyethyl)-p-phenylenediamine, N-(2-methoxyethyl)-p-phenylenediamine, 2,3-, 2,4- or 2,5-dichloro-p-phenylenediamine, 2-chloro-p-phenylenediamine, 2,5-dihydroxy-4-morpholinoaniline dihydrobromide, 2-, 3- or 4-aminophenol, 2-aminomethyl-4-aminophenol, 2-hydroxymethyl-4-aminophenol, ortho-phenylenediamine, p-phenylenediamine, ortho-toluenediamine, 2,5-diaminotoluene, 2,5-diaminophenol, 2,5-diaminophenethol, 4-amino-3-methylphenol, 2-(2,5-diaminophenyl)ethanol, 2,4-diaminophenoxyethanol, 2-(2,5-diaminophenoxy)ethanol, 4-methylaminoaniline, 3-amino-4-(2'-hydroxyethyloxy)aniline, 3,4-methylenediaminoaniline, 3,4-methylenedioxyaniline, 3-amino-2,4-dichlorophenol, 4-methylaminophenol, 2-methyl-5-aminophenol, 3-methyl-4-aminophenol, 2-methyl-5-(2-hydroxyethylamino)phenol, 6-methyl-3-amino-2-chlorophenol, 2-methyl-5-amino-4-chlorophenol, 3,4-methylenedioxyphenol, 5-(2-hydroxyethylamino)-4-methoxy-2-methylphenol, 4-amino-2-hydroxymethylphenol, 1,3-diamino-2,4-dimethoxybenzene, 2-, 3- or 4-aminobenzoic acid, 2-amino-, 3-amino- or 4-aminophenylacetic acid, 2,3-, 2,4-, 2,5-, 3,4- or 3,5-diaminobenzoic acid, 4-amino- or 5-aminosalicylic acid, 3-amino-4-hydroxybenzoic acid, 4-amino-3-hydroxybenzoic acid, 2-amino, 3-amino- or 4-aminobenzenesulphonic acid, 3-amino-4-hydroxybenzenesulphonic acid, 4-amino-3-hydroxynaphthalene-1-sulphonic acid, 6-amino-7-hydroxynaphthalene-2-sulphonic acid, 7-amino-4-hydroxynaphthalene-2-sulphonic acid, 4-amino-5-hydroxynaphthalene-2, 7-disulphonic acid, 3-amino-2-naphthoic acid, 3-aminophthalic acid, 5-aminoisophthalic acid, 1,3,5-triaminobenzene, 1,2,4-triaminobenzene, 1,2,4,5-tetraaminobenzene, 2,4,5-triaminophenol, pentaaminobenzene, hexaaminobenzene, 2,4,6-triaminoresorcinol, 4,5-diaminopyrocatechol, 4,6-diaminopyrogallol, 3,5-diamino-4-hydroxypyrocatechol, and aromatic anilines and aromatic phenols comprising an aromatic residue of formula (II):

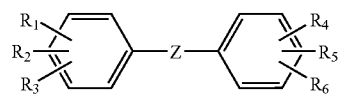

wherein:

$R_1$ is chosen from hydroxyl and amino radicals optionally substituted with a radical chosen from $C_{1-4}$ alkyl, $C_{1-4}$ hydroxyalkyl and ($C_{1-4}$ alkoxy)($C_{1-4}$ alkyl) radicals, $R_2$, $R_3$, $R_4$, $R_5$ and $R_6$, which may be identical or different, are chosen from a hydrogen atom, hydroxyl radicals and amino radicals, optionally substituted with a radical chosen from $C_{1-4}$ alkyl, $C_{1-4}$ hydroxyalkyl, ($C_{1-4}$ alkoxy)($C_{1-4}$ alkyl), carboxylic acid and sulphonic acid radicals, Z is chosen from a direct bond; saturated and unsaturated, $C_{1-4}$ hydrocarbon-based radicals optionally hydroxylated; carbonyl radicals; sulphonyl radicals; imino radicals; oxygen atoms; sulphur atoms; and radicals of formula Q-($CH_2$—P—$CH_2$-Q')$_o$, wherein "$o$" is a number ranging from 1 to 4, P is chosen from a direct bond, —$CH_2$— radicals and —CHOH— radicals, Q and Q', which may be identical or different, are chosen from oxygen atoms, $NR^7$ radicals wherein $R^7$ is chosen from a hydrogen atom, $C_{1-4}$ alkyl and $C_{1-4}$ hydroxyalkyl radicals, O—($CH_2$)$_p$NH radicals and NH—($CH_2$)$_p$'—O radicals, wherein p and p' are equal to 2 or 3.

8. The process according to claim 6, wherein the at least one compound comprising a primary or secondary amine functional group is an aliphatic amine chosen from 2-aminoethanol, 2-methoxyethylamine, 2-ethoxyethylamine, 2-(2-aminoethoxy)ethanol, 2- or 3-aminopropanol, 2,3-dihydroxypropylamine, 4-hydroxypropylamine, 2-aminopropane-1,3-diol, 2-amino-2-methylpropanol, 2-amino-2-methylpropane-1,3-diol, 2-amino-2-hydroxymethylpropane-1,3-diol, tetrahydropentylamine, pentahydroxyhexylamines, glucamine, D-glucosamine, D-galactosamine, 1,2-diaminoethane, 1,2- or 1,3-diaminopropane, 1,3-diamino-2-propanol, 2-(2-aminoethylamino)ethylamine, 2-(2-aminoethylamino)ethanol, 3-(2-aminoethylamino)propylamine, and 3-(2-aminoethylamino)propanol.

9. The process according to claim 6, wherein the at least one compound comprising an activated methylene functional group is chosen from 1,2,3,3-tetramethyl-3H-indolium iodide, 1,2,3,3-tetramethyl-3H-indolium p-toluenesulphonate, 1,2,3,3-tetramethyl-3H-indolium methanesulphonate, 1,3,3-trimethyl-2-methyleneindoline, 2,3-dimethylbenzothiazolium iodide, 2,3-dimethylbenzothiazolium p-toluenesulphonate, rhodanine, rhodanine-3- acetic acid, 1-ethyl-2-quinaldinium iodide, 1-methyl-2-quinaldinium iodide, barbituric acid, thiobarbituric acid, 1,3-dimethylthiobarbituric acid, diethylthiobarbituric acid, oxindole, 3-indoxyl acetate, coumarone and 1-methyl-3-phenyl-2-pyrazolinone.

10. The process according to claim 1, wherein the composition has a pH ranging from 2 to 12.

11. The process according to claim 10, wherein the composition has a pH ranging from 3 to 11.

12. The process according to claim 1, wherein the at least one ninhydrin compound of formula (I) is present in the composition in an amount ranging from 0.0001% to 30% by weight, relative to the total weight of the composition.

13. The process according to claim 6, wherein the at least one compound chosen from compounds comprising an activated methylene functional group and compounds comprising a primary or secondary amine functional group is present in the composition in an amount ranging from 0.0001% to 30% by weight, relative to the total weight of the composition.

14. The process according to claim 1, wherein the composition further comprises at least one surfactant and/or polymer of nonionic, cationic, anionic or amphoteric nature.

15. A cosmetic dye composition comprising, in a medium that is suitable for dyeing keratin fibers, at least one ninhydrin compound of formula (I) or the tautomer thereof:

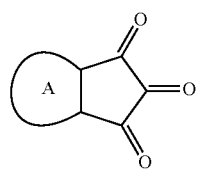

(I)

wherein:
A is chosen from fused and non-fused, aromatic mono- and polyheterocyclic group comprising at least 5-members, and at least one hetero atom chosen from nitrogen, oxygen, sulfur and/or phosphorus; and
at least one surfactant and/or polymer of nonionic, cationic, anionic or amphoteric nature.

16. A ready-to-use cosmetic composition comprising at least one ninhydrin compound of formula (I) or the tautomer thereof:

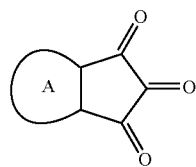

(I)

wherein:
A is chosen from fused and non-fused, aromatic mono- and polyheterocyclic groups comprising at least 5-members, and at least one hetero atom chosen from nitrogen, oxygen, sulfur and/or phosphorus; and
at least one compound chosen from compounds comprising a primary or secondary amine functional group and compounds comprising an activated methylene functional group.

17. A multi-component coloring agent comprising
at least one first component comprising a composition comprising at least one ninhydrin compound of formula (I) or the tautomer thereof:

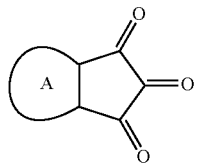

(I)

wherein:
A is chosen from fused and non-fused, aromatic mono- and polyheterocyclic groups comprising at least 5-members, and at least one hetero atom chosen from nitrogen, oxygen, sulfur and/or phosphorus; and
at least one second component, comprising a composition comprising at least one activator chosen from oxidizing agents, reducing agents, Brönsted acids, metal catalysts, proteins, compounds that modify the ionic strength of the medium, and compounds comprising at least one labile hydrogen chosen from those comprising a primary or secondary amine functional group and those comprising an activated methylene functional group.

18. A multi-compartment kit, comprising
at least one first compartment comprising a composition comprising at least one ninhydrin compound of formula (I) or the tautomer thereof:

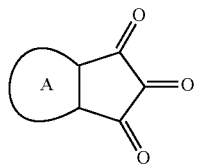

(I)

wherein:
A is chosen from fused and non-fused, aromatic mono- and polyheterocyclic groups comprising at least 5-members, and at least one hetero atom chosen from nitrogen, oxygen, sulfur and/or phosphorus; and
at least one second compartment comprising at least one second component, comprising a composition comprising at least one activator chosen from oxidizing agents, reducing agents, Brönsted acids, metal catalysts, proteins, compounds that modify the ionic strength of the medium, and compounds comprising at least one labile hydrogen chosen from those comprising a primary or secondary amine functional group and those comprising an activated methylene functional group.

19. The process according to claim 1, wherein the composition applied to the keratin materials is left on the keratin materials for a leave-in time that is sufficient to obtain the desired coloration, followed by the rinsing and washing of the keratin materials.

20. The process according to claim 19, wherein the keratin materials impregnated with hair dye composition are heated to a temperature of less than or equal to 80° C.

21. The process according to claim 20, wherein the temperature is less than or equal to 60° C.

22. A process for dyeing hair comprising the successive application to the hair, one after the other, in any order, of the at least one first component and the at least one second component as defined in claim 17.

23. The process according to claim 22, further comprising rinsing the hair between the application of the at least one first or second component and the application of the at least one first or second component.

24. The process according to claim 22, comprising heating the hair impregnated with either the at least one first and/or at least one second component to a temperature of less than or equal to 80° C.

25. The process according to claim 24, wherein the impregnated hair is heated to a temperature of less than or equal to 60° C.

* * * * *